Jan. 15, 1957 E. S. BOERNER Plant Pat. 1,553
CHRYSANTHEMUM PLANT
Filed Feb. 27, 1956
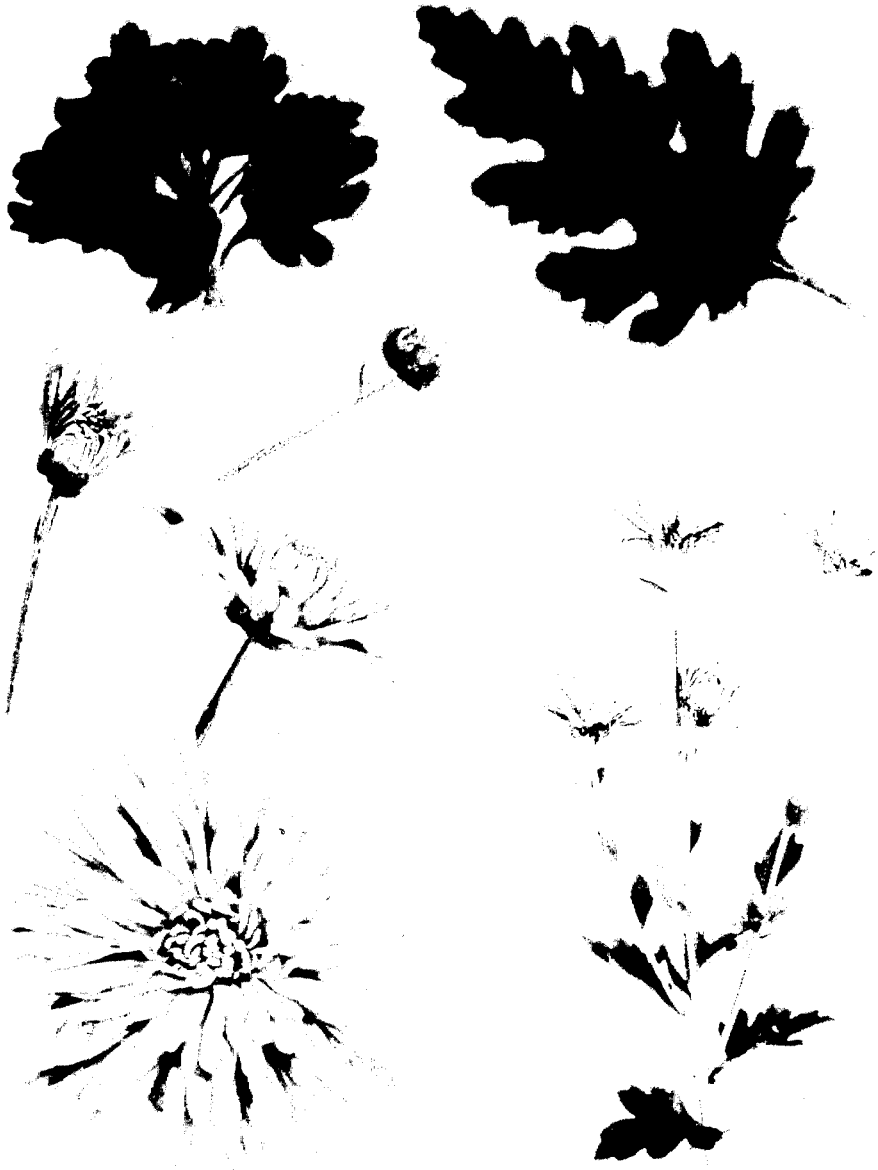
Inventor.
E. S. Boerner
By: Robb & Robb
Attorneys.

United States Patent Office

Plant Pat. 1,553
Patented Jan. 15, 1957

1,553

CHRYSANTHEMUM PLANT

Eugene S. Boerner, Newark, N. Y., assignor to Jackson & Perkins Company, Newark, N. Y., a corporation of New York Application February 27, 1956, Serial No. 568,130

1 Claim. (Cl. 47—60)

The present invention relates to a new and distinct variety of chrysanthemum plant of the semi-decorative type, which was originated by me by crossing the variety "Fred Rockwell" (Plant Patent No. 718) with an unnamed and unpatented large-flowered Hortorum seedling.

The primary objective in making this cross was to produce a new chrysanthemum variety in the "Fred Rockwell" color range, but which bears larger flowers than those of said "Fred Rockwell" variety. This objective was fully achieved, along with other improvements and advantages, as evidenced by the fact that the flowers of the new variety are relatively large; the general color tonality of the flowers is Bittersweet Orange, lightly overcast with Grenadine Red; the plant growth is free and airy; and its foliage is leathery.

The foregoing characteristics and distinctions definitely differentiate my new variety from its parents, as well as from all other varieties of its class of which I am aware, and asexual reproduction thereof by both top cuttings and underground runners, as performed by me at Newark, New York, shows that these characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character, together with a typical plant specimen depicting in black-and-white its characteristic upright, free and airy growth.

The following is a detailed description of my new variety, with color terminology in accordance with Ridgway's Color Standards and Nomenclature:

Parentage: "Fred Rockwell" × an unnamed large-flowered Hortorum seedling.
Classification: Semi-decorative type.
Growth: From 25 inches to 30 inches tall.
Cold resistance: Winter hardy in northern New York; flowers are very frost resistant, as compared with other varieties grown under comparable cultural conditions in Newark, New York, area.

Blooming period: In the Newark, New York, climatic area, blooming begins about September 15th, and continues until heavy frosts.

FLOWER (Observations made from specimens grown in a field at Newark, New York in the early part of October, and in the early afternoon.)

Bud:
- *Color.*—When sepals first divide—Onion-skin Pink, Plate 28. When petals begin to unfurl—Capucine Buff, Plate 3, lightly overcast with Scarlet, Plate 1. When half-blown: Inside of petals—Grenadine, Plate 2, lightly overcast with Scarlet, Plate 1 on the outer edge of the petal; outside of petals—Pale Yellow-Orange, Plate 3, lightly overcast with Carnelian Red, Plate 14.
- *Peduncle.*—Very long; very strong. Color—Light Bice Green, Plate 17.

Bloom:
- *Size.*—From 3½ inches to 4 inches.
- *Stem.*—Long; strong.
- *Form.*—Semi-decorative.
- *Petalage.*—Full-double.
- *Color.*—Center of flower—Scarlet, Plate 1. Outer petals—Apricot Buff, Plate 14, slightly overcast with Bittersweet Pink, Plate 2. Base of petals—Sulphur Yellow, Plate 5. Inside of petals—Bittersweet Orange, Plate 2, lightly overcast with Grenadine Red, Plate 2. Reverse of petals—Pale Yellow-Orange, Plate 3.
- *Petals.*—Texture—stiff. Form—long-pointed.
- *Fragrance.*—Characteristic chrysanthemum.

PLANT

Form: Upright.
Growth: Free and airy.
Foliage:
- *Size.*—Small.
- *Quantity.*—Normal.
- *Color.*—Upper side—Forest Green, Plate 17; reverse side—Cress Green, Plate 31.
- *Texture.*—Leathery; clean.

I claim:

A new and distinct variety of chrysanthemum plant of the semi-decorative type, substantially as herein shown and described, characterized particularly as to novelty by its free and airy growth, its leathery foliage, and the Bittersweet Orange, lightly overcast with Grenadine Red, general color tonality of its flowers, and their relatively large size.

No references cited.